(12) United States Patent
Karim et al.

(10) Patent No.: US 9,422,204 B2
(45) Date of Patent: Aug. 23, 2016

(54) PROCESS FOR PRODUCING ETHYLENE AND PROPYLENE FROM SYNGAS

(71) Applicants: Khalid Karim, Riyadh (SA); Labeeb Chaudhary Ahmed, Riyadh (SA)

(72) Inventors: Khalid Karim, Riyadh (SA); Labeeb Chaudhary Ahmed, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/005,973

(22) PCT Filed: Jun. 25, 2013

(86) PCT No.: PCT/EP2013/063307
§ 371 (c)(1),
(2) Date: Sep. 18, 2013

(87) PCT Pub. No.: WO2014/001350
PCT Pub. Date: Jan. 3, 2014

(65) Prior Publication Data
US 2014/0128486 A1    May 8, 2014

(30) Foreign Application Priority Data

Jun. 25, 2012 (EP) ..................................... 12004731

(51) Int. Cl.
| C07C 1/00 | (2006.01) |
| C07C 1/04 | (2006.01) |
| C07C 6/04 | (2006.01) |
| C07C 4/02 | (2006.01) |
| B01J 37/03 | (2006.01) |
| B01J 23/00 | (2006.01) |
| B01J 27/187 | (2006.01) |
| C10G 45/68 | (2006.01) |
| C10G 2/00 | (2006.01) |

(52) U.S. Cl.
CPC ............ C07C 1/0435 (2013.01); B01J 23/005 (2013.01); B01J 27/187 (2013.01); B01J 37/031 (2013.01); C07C 4/02 (2013.01); C07C 6/04 (2013.01); C10G 2/332 (2013.01); C10G 45/68 (2013.01); C07C 2523/10 (2013.01); C07C 2523/28 (2013.01); C07C 2523/30 (2013.01); C07C 2523/34 (2013.01); C07C 2523/36 (2013.01); C07C 2523/75 (2013.01); C10G 2400/20 (2013.01); Y02P 20/52 (2015.11)

(58) Field of Classification Search
CPC ...... C07C 1/0435; C07C 11/04; C07C 11/06; C07C 2523/75; C07C 2523/34; C07C 2523/30; C07C 2523/28; C07C 2523/10; C10G 2/332; C10G 2400/20; C10G 2400/22
USPC .......................................... 518/715; 585/324
See application file for complete search history.

(56) References Cited

U.S. PATENT DOCUMENTS

| 3,932,552 | A | 1/1976 | Starks | |
| 4,131,568 | A | 12/1978 | Bartish | |
| 4,177,203 | A | 12/1979 | Kolbel et al. | |
| 4,451,579 | A | 5/1984 | Lemanski et al. | 502/306 |
| 5,248,701 | A | 9/1993 | Soled et al. | 518/700 |
| 5,958,985 | A | 9/1999 | Geerlings et al. | 518/700 |
| 5,981,608 | A | 11/1999 | Geerlings et al. | 518/715 |
| 5,990,369 | A | 11/1999 | Barger et al. | |
| 6,586,649 | B1 | 7/2003 | Botha et al. | |
| 7,253,136 | B2 | 8/2007 | Mauldin et al. | 502/327 |
| 7,365,040 | B2 | 4/2008 | Van Berge et al. | 502/260 |
| 7,375,055 | B2 | 5/2008 | Van Berge et al. | 502/332 |
| 8,153,851 | B2 | 4/2012 | Gartside et al. | |
| 2001/0006984 | A1 | 7/2001 | Lapidus | 518/709 |
| 2002/0010221 | A1 | 1/2002 | Ionkina et al. | |
| 2003/0027874 | A1 | 2/2003 | Herron et al. | 518/713 |
| 2005/0113463 | A1 | 5/2005 | O'Rear et al. | |
| 2008/0033218 | A1 | 2/2008 | Lattner et al. | 568/897 |
| 2008/0262114 | A1 | 10/2008 | Reynhout | |
| 2010/0069589 | A1* | 3/2010 | Bradin | 526/170 |
| 2012/0083539 | A1* | 4/2012 | Fu et al. | 518/713 |
| 2012/0115967 | A1 | 5/2012 | Bezemer et al. | |

FOREIGN PATENT DOCUMENTS

| CN | 201180065826 | 12/2011 |
| CN | 102500425 A | 6/2012 |
| CN | 2013800320200 | 6/2013 |

(Continued)

OTHER PUBLICATIONS

Commereuc D, et al. (1980) Catalytic synthesis of low molecular weight olefins from Co and H2 with Fe(Co)5, Fe3(Co)12, and [HFe3(Co)11]-supported on inorganic oxides. J.C.S. Chem. Comm.: 154-155.

(Continued)

Primary Examiner — Jafar Parsa (74) Attorney, Agent, or Firm — Ballard Spahr LLP (57) ABSTRACT

The present invention relates to a process for producing ethylene and propylene from syngas, the process comprising the steps of a) contacting syngas (2) with a first catalyst composition to obtain a first product stream (3) comprising ethylene, propylene and aliphatic hydrocarbons having 4 or more carbon atoms, b) splitting the first product stream (3) into a second product stream (5) comprising at least 90% of said aliphatic hydrocarbons having 4 or more carbon atoms and a third product stream (4) comprising ethylene and propylene, 3) separating ethylene and propylene in the third product stream so as to form a first ethylene stream (17) and a first propylene stream (16) and d) converting the second product stream (5) into a fourth product stream (8) comprising ethylene and/or propylene.

14 Claims, 2 Drawing Sheets

(56) References Cited

FOREIGN PATENT DOCUMENTS

| | | |
|---|---|---|
| CN | 2013800320215 | 6/2013 |
| EA | 201300736 | 12/2011 |
| EA | 201590086 | 6/2013 |
| EA | 201590105 | 6/2013 |
| EP | 1970361 A1 | 9/2008 |
| EP | 10015923.5 | 12/2010 |
| EP | 11802287.0 | 12/2011 |
| EP | 2422876 A1 | 2/2012 |
| EP | 12004731.1 | 6/2012 |
| EP | 13731348.2 | 6/2013 |
| EP | 13734700.1 | 6/2013 |
| GC | GCC/P/2011/20076 | 12/2011 |
| GC | 2013-24762 | 6/2013 |
| GC | 2013-24763 | 6/2013 |
| IN | 6320/DELNP/2013 | 12/2011 |
| JP | S 59179154 A | 10/1984 |
| JP | 2007-512328 A | 5/2007 |
| JP | 2013-545093 | 12/2011 |
| TH | 1301003512 | 12/2011 |
| WO | WO 01/76736 | 10/2001 |
| WO | WO-03/041860 A2 | 5/2003 |
| WO | WO-03/076074 A1 | 9/2003 |
| WO | PCT/EP2011/006374 | 12/2011 |
| WO | WO 2012/084160 A1 | 6/2012 |
| WO | PCT/EP2013/063307 | 6/2013 |
| WO | PCT/EP2013/063311 | 6/2013 |
| WO | WO 2014/001350 | 1/2014 |
| WO | WO 2014/001354 | 1/2014 |

OTHER PUBLICATIONS

Colley S, et al. (1988) Carbon monoxide hydrogenation using cobalt manganese oxide catalysts: initial catalyst optimization studies. Ind. Eng. Chem. Res., 27: 1339-1344.

Dry M, et al. (2004) Stud. Surf. Sci. Catal., 152: 197-230.

Keyser MJ, et al. (1998) Fischer-Tropsch studies with cobalt-manganese oxide catalysts: Synthesis performance in a fixed bed reactor. Applied Catalysis, 171: 99-107.

Mirzaei, et al. (2009) Fischer-Tropsch Synthesis over Iron Manganese Catalysts: Effect of Preparation and Operating Conditions on Catalyst Performance Adv. Phys. Chem., 2009: 1-12.

Okuhara T, et al. (1981) Synthesis of Light Olefins from Co and H2 over Highly Dispersed Ru/K-Al2O3 derived from RU3(Co)12. J.C.S. Chem. Comm.: 114-1115.

Van der Riet M, et al. (1986) Selective formation of C3 hydrocarbons from co + H2 using cobalt-manganese oxide catalysts. J.C.S. Chem. Commun.: 798-799.

International Search Report and Written Opinion mailed on Oct. 2, 2013 for Intl. Pat. App. No. PCT/EP2013/063307 filed Jun. 25, 2013 and published as WO 2014/001350 on Jan. 3, 2014 (Applicants—Saudi Basic Industries Corporation; Inventors—Karim et al.; (10 pages).

Extended European Search Report issued on Aug. 30, 2012 for European Pat. App. No. 12004731.1 filed Jun. 25, 2012 (Applicant—Saudic Basic Industries Corporation; Inventors—Karim et al.

Liu Xijing et al., Effect of isomorphic substitution of lanthanum on mesoporous silica as support for Co Fisher-Tropsch synthesis catalysts, Journal of Guizhou University (Natural Science), vol. 27, No. 3, pp. 25-27 (2010).

First Office Action issued May 29, 2014 from the CCPIT Patent and Trademark Law Office for Chinese Application 201180065826, filed Dec. 15, 2011 (Applicant: Saudi Basic Indus. Corp.//1st Named Inventor: Karim//.

International Search Report and Written Opinion mailed on Oct. 2, 2013 for Intl. Pat. App. No. PCT/EP2013/063307 filed Jun. 25, 2013 and published as WO 20141001350 (Applicant: Saudi Basic Indus. Corp.//1st Named Inventor: Karim// (10 pages).

Extended European Search Report mailed Apr. 18, 2011 for Application No. 10015923.5 (Applicant: Saudi Basic Indus. Corp.//1st Named Inventor: Karim// (6 pages).

International Search Report and Written Opinion mailed Jan. 31, 2012 for Application No. PCT/EP2011/006374, which was filed Dec. 15, 2011 and published as WO 2012/084160 (Applicant: Saudi Basic Indus. Corp.//1st Named Inventor: Karim// (10 pages).

International Search Report and Written Opinion mailed Oct. 10, 2013 for Application No. PCT/EP2013/063311 which was filed Jun. 25, 2013 and published as WO 2014/001354 (Applicant: Saudi Basic Indus. Corp.//1st Named Inventor: Karim// (9 pages).

Non Final Office Action mailed Jan. 2, 2015 for U.S. Appl. No. 13/995,646, which was filed Jun. 19, 2013 and published as US 2013/0274355 A (Applicant: Saudi Basic Indus. Corp.//1st Named Inventor: Karim// (9 pages).

U.S. Appl. No. 13/995,646, filed Dec. 15, 2011 Karim (Saudi Basic Industries).

U.S. Appl. No. 14/409,017, filed Jun. 25, 2013 Karim (Saudi Basic Industries).

U.S. Appl. No. 61/665,005, filed Jun. 27, 2012 Karim (Saudi Basic Industries).

Notice of Allowance issued on May 6, 2016 for U.S. Appl. No. 13/995,646, filed Jun. 19, 2013 and published as U.S. Pat. No. 2013-0274355-A1 on Oct. 17, 2013 (Applicant—Saudi Basic Industries Corporation//Inventor—Karim) (8 pages).

\* cited by examiner

PROCESS FOR PRODUCING ETHYLENE AND PROPYLENE FROM SYNGAS

CROSS REFERENCE TO RELATED APPLICATIONS

The present application is a National Phase Application of International Application No. PCT/EP2013/063307, filed Jun. 25, 2013, which claims priority to European Patent Application No. 12004731.1, filed Jun. 25, 2012, which applications are incorporated herein fully by this reference.

The present invention relates to a process for producing ethylene and propylene from syngas using a catalyst composition.

Gaseous mixtures comprising hydrogen ($H_2$) and carbon monoxide (CO) can be converted into a hydrocarbon product stream by a catalytic process known as Fischer-Tropsch synthesis (F-T synthesis). The most common catalysts useful in F-T synthesis ("F-T catalysts") are based on Fe and/or Co, although Ni- and Ru-based catalysts have also been described (see e.g. U.S. Pat. No. 4,177,203; Commereuc (1980) J. Chem. Soc., Chem. Commun. 154-155; Okuhara (1981) J. Chem. Soc., Chem. Commun. 1114-1115). Generally, Ni-based catalysts are relatively more selective for producing methane whereas Co-, Fe- and Ru-based catalysts are more selective for hydrocarbons having at least two carbon atoms (C2+ hydrocarbons). Moreover, the selectivity for C2+ hydrocarbons can be increased by decreasing the $H_2$:CO ratio, decreasing the reaction temperature and decreasing the reactor pressure.

It has been previously described that unsupported cobalt-manganese oxide catalysts can be used as an F-T catalyst having an improved selectivity for C3 hydrocarbons and a suppressed $CH_4$ selectivity (see Van der Riet (1986) J. Chem. Soc. Chem. Commun 798-799 and Keyser (1998) Applied Catalysis 171:99-107). The unsupported cobalt-manganese oxide composition suitable for use as F-T catalyst was produced by a process comprising the steps of co-precipitating cobalt and manganese oxides from cobalt- and manganese-comprising solution, calcining the precipitate to form a calcined catalyst precursor and reducing the calcined catalyst precursor to obtain the cobalt-manganese oxide catalyst composition (see Colley (1988) Ind. Eng. Chem. Res. 27:1339-1344). It was found that the catalyst precursor comprised the mixed spinels $Co_2MnO_4$ and $Co_2Mn_2O_4$. Reduction of the catalyst precursor resulted in an unsupported catalyst composition comprising metallic Co, MnO and a certain amount of mixed spinels $Co_2MnO_4$ and $Co_2Mn_2O_4$.

It was the disadvantage of the prior art that F-T synthesis of hydrocarbon products always result in a mixture of desired products and less desired products.

Furthermore, conventional unsupported cobalt-manganese oxide F-T catalysts has a drawback due to their relatively low activity resulting in a relatively low syngas conversion rate.

It was an object of the present invention to provide an improved process for producing a higher yield of ethylene and propylene from syngas.

The solution to the above problem is achieved by providing the embodiments as described herein below and as characterized in the claims. Accordingly, the present invention provides a process for producing ethylene and propylene from syngas, the process comprising the steps of a) contacting syngas with a first catalyst composition to obtain a first product stream comprising ethylene, propylene and aliphatic hydrocarbons having 4 or more carbon atoms, b) splitting the first product stream into
   a second product stream comprising at least 90% of said aliphatic hydrocarbons having 4 or more carbon atoms and
   a third product stream comprising ethylene and propylene, c) separating ethylene and propylene in the third product stream so as to form a first ethylene stream and a first propylene stream, d) converting the second product stream into a fourth product stream comprising ethylene and/or propylene.

Integrated Process

In the process according to the present invention, the syngas is first contacted with a first catalyst composition to be converted to a first product stream, preferably by Fischer-Tropsch synthesis. The first product stream comprises ethylene, propylene and aliphatic hydrocarbons having 4 or more carbon atoms.

The first product stream may further comprise other components such as methane, ethane, propane, aromatic hydrocarbons and $CO_2$.

Preferably, the aliphatic hydrocarbons having 4 or more carbon atoms essentially consist of aliphatic hydrocarbons having 4-10 carbon atoms, more preferably 4-8 carbon atoms, more preferably 4-6 carbon atoms. The term "essentially consist of" in this context may mean at least 95 wt %, at least 99 wt % or at least 99.5 wt %.

The aliphatic hydrocarbons having 4 or more carbon atoms may comprise e.g. butane, butene, pentane, pentene, hexane and hexene. The aliphatic hydrocarbons having 4 or more carbon atoms preferably comprise 1-butene and 1-hexene.

The first product stream is split into two product streams: a product stream of aliphatic hydrocarbons having 4 or more carbon atoms and a product stream of aliphatic hydrocarbons having 3 or less carbon atoms. This step may be done by a depropanizer, which is well-known to the skilled person.

The first product stream is split into a second product stream comprising at least 90 wt % of said aliphatic hydrocarbons having 4 or more carbon atoms and a third product stream comprising ethylene and propylene. The second product stream preferably comprises at least 95 wt %, more preferably at least 99 wt % or more preferably at least 99.5 wt % of said aliphatic hydrocarbons having 4 or more carbon atoms. The remainder of the second product stream is the component of the first product stream. Most preferably, the third product stream consists of the aliphatic hydrocarbons having 4 or more carbon atoms.

The third product stream comprises no or little amount of aliphatic hydrocarbons having 4 or more carbon atoms. The third product stream preferably comprises at most 10 wt %, more preferably at most 5 wt %, more preferably at most 1 wt % or more preferably at most 0.5 wt % of the aliphatic hydrocarbons having 4 or more carbon atoms. Most preferably, the third product stream does not comprise the aliphatic hydrocarbons having 4 or more carbon atoms.

The third product stream comprises ethylene and propylene. In the cases where the third product stream comprises other components, said other components are preferably mostly other aliphatic hydrocarbons having 3 or less carbon atoms such as methane, ethane and propane. Preferably, the third product stream comprises at least 90 wt %, more preferably at least 95 wt %, more preferably at least 99 wt % or more preferably at least 99.5 wt % of aliphatic hydrocarbons having 3 or less carbon atoms.

Preferably, a large portion of the third product stream is ethylene and propylene. The third product stream preferably comprises at least 30 wt %, more preferably at least 50 wt %, more preferably at least 75 wt %, more preferably at least 90 wt % of ethylene and propylene.

Ethylene and propylene are separated from the third product stream so as to form a first ethylene stream and a first propylene stream.

Further, the second product stream is converted into a fourth product stream comprising ethylene and/or propylene. The fourth product stream may be split into a second ethylene stream and a second propylene stream. The first and second ethylene and/or the first and second propylene stream may be combined.

The process according to the present invention has an advantage that ethylene and propylene are obtained in two ways. Ethylene and propylene are directly obtained from the syngas by a conversion using the first catalyst composition. Furthermore, the aliphatic hydrocarbons having 4 or more carbon atoms from the first product stream is converted to ethylene and/or propylene. Hence, the process according to the present invention results in an overall high yield of ethylene and/or propylene.

Preferably, the fourth product stream comprising ethylene and/or propylene is mixed with the first product stream. This may be done by feeding said fourth product stream back to the unit for splitting the first product stream into the second and the third product streams, e.g. depropanizer. During the conversion of the second product stream, aromatics may also be produced, mainly benzene, toluene and xylene. Before the fourth product stream is mixed with the first product stream, these aromatics are preferably separated from the fourth product stream.

The first product stream may further comprise methane, ethane and propane. In this case, methane, ethane and propane in the first product stream are preferably included in the third product stream by the splitting step of the first product stream. In this case, step c) preferably comprises the steps of:

c1) removing methane from the third product stream to obtain a fifth product stream comprising ethane, ethylene, propane and propylene, c2) separating the fifth product stream into a sixth product stream comprising ethane and ethylene and a seventh product stream comprising propane and propylene, c3) removing ethane from the sixth product stream to form the first ethylene stream and c3') removing propane from the seventh product stream to form the first propylene stream, In step c1), methane is removed from the third product stream. The remaining product stream, i.e. the fifth product stream comprises ethane, ethylene, propane and propylene and preferably comprises low amount of methane. The fifth product stream preferably comprises at most 10 wt %, at most 5 wt %, at most 1 wt % or at most 0.5 wt % of methane. The fifth product stream preferably comprises at least 90 wt %, more preferably at least 95 wt %, more preferably at least 99 wt % or more preferably at least 99.5 wt % of ethane, ethylene, propane and propylene. This step may be done by a demethanizer, which is well-known to the skilled person.

Subsequently, the fifth product stream is separated into a six product stream comprising ethane and ethylene and a fifth product stream comprising propane and propylene in step c2). This may be done by a deethanizer, which is well-known to the skilled person. The sixth product stream preferably comprises at least 90 wt %, more preferably at least 95 wt %, more preferably at least 99 wt % or more preferably at least 99.5 wt % of ethane and ethylene. The seventh product stream preferably comprises at least 90 wt %, more preferably at least 95 wt %, more preferably at least 99 wt % or more preferably at least 99.5 wt % of propane and propylene.

Subsequently, the sixth product stream is separated into ethane and ethylene e.g. by a C2 splitter and the seventh product stream is separated into propane and propylene e.g. by a C3 splitter.

Preferably, propane removed from the seventh product stream in step c3') is dehydrogenated into propylene and mixed with the seventh product stream. The propylene obtained may be fed back to the C3 splitter. This results in an even higher overall yield of propylene. Suitable ways for dehydrogenation of propane into propylene is well-known to the skilled person.

Preferably, methane removed from the third product stream of step c1) is added to the syngas. This stream comprising methane may be collected from the demethanizer into a recycle unit and fed from the recycle unit to the syngas generation unit for feeding the syngas. Similarly, ethane removed from the sixth product stream in step c3) is preferably added to the syngas. Ethane may be collected from the C2 splitter into a recycle unit and fed from the recycle unit to the syngas generation unit for feeding the syngas. The recycle unit for collecting methane and ethane may be the same unit and may mix methane and ethane before feeding the mixture gas to the syngas generation unit.

First Catalyst Composition

Preferably, the first catalyst composition is unsupported and comprises cobalt; manganese; and at least one element selected from the group of lanthanum and phosphorus, wherein the relative molar ratios of the elements comprised in said composition are represented by the formula $$CoMn_aLa_bP_cM_dO_x$$

wherein:

M is one or more elements selected from the group consisting of alkali metal, alkaline earth metal and transition metal;

a is about 0.8-1.2;

b and/or c is >0-about 0.005;

d is 0-about 0.005; and x is a number determined by the valence requirements of the other elements present.

This type of first catalyst composition shows a surprisingly high activity resulting in a high ratio of ethylene and propylene in the first product stream.

It is noted that US2002/010221 discloses a catalyst useful for the production of hydrocarbons from synthesis gas in the Fischer-Tropsch reaction. The catalyst comprises cobalt and rhenium; and a promoter selected from the group consisting of boron, phosphorous, vanadium, manganese, and alkali metals. The catalyst is supported e.g. on an alumina support.

In the context of the present invention, it was surprisingly found that the catalyst activity of a conventional cobalt manganese oxide FT-catalyst can be significantly increased when said conventional catalyst is modified with La and/or P and optionally one or more elements selected from the group consisting of alkali metal, alkaline earth metal and transition metal. Furthermore, it was found that the first catalyst composition of the present invention has a decreased selectivity for $CO_2$ and $CH_4$ which are unwanted side products of F-T synthesis. Hence, the first catalyst composition used in the present invention is particularly suitable for converting a syngas into a hydrocarbon comprising product stream.

The first catalyst composition is a lanthanum and/or phosphorus-modified unsupported cobalt manganese oxide catalyst which, after calcination and reduction, comprises a mixture comprising metallic Co, MnO and the mixed spinels $Co_2MnO_4$ and $Co_2Mn_2O_4$. In addition thereto, the unsupported cobalt manganese oxide catalyst of the present invention may be modified with one or more elements selected from the group consisting of alkali metal, alkaline earth metal and transition metal.

The molar ratio of Co:Mn is about 1:0.8-1.2 (depicted as: $CoMn_a$ wherein a is 0.8-1.2). This means that the molar ratio of Co:Mn is between about 1:0.8: and about 1:1.2. More preferably, the molar ratio of Co:Mn is about 1:0.9-1.1. Most preferably, the molar ratio of Co:Mn is about 1:1. The molar ratio of Co:Mn appears to be very important to obtain a catalyst composition having a high light olefin selectivity and a low methane selectivity. The relative ratio of cobalt and manganese has a strong effect on selectivity of the catalyst for hydrocarbons. When the Co:Mo ratio is too high, the hydrogenation activity of the catalyst is increased leading to an increased methane selectivity.

The first catalyst composition used in the present invention comprises at least one element selected from the group consisting of lanthanum and phosphorus. In one embodiment, accordingly, the catalyst comprises lanthanum but does not comprise phosphorus. In one embodiment, the catalyst comprises phosphorus but does not comprise lanthanum. In one preferred embodiment, the catalyst comprises both lanthanum and phosphorus.

The amount of lanthanum and/or phosphorus present in the first catalyst composition is determined by the molar ratio of the cobalt in relation to said lanthanum and/or phosphorus in the catalyst composition. The molar ratio of Co:"at least one element selected from the group consisting of La and P" ("Co:La and/or P") is 1:>0-about 0.005 (depicted as $CoLa_bP_b$ wherein b and/or c is >0-about 0.005). The term ">0" means that said element must be present in the catalyst composition.

In case the first catalyst composition comprises La, the molar ratio Co:La is up to 1:about 0.005 (1:about 5E-3; also depicted as: $CoLa_b$ wherein b is >0-about 0.005) and preferably up to 1:about 1E-3. Preferably, the molar ratio of Co:La is at least 1:about 1E-6 in case the first catalyst composition comprises La, more preferably at least 1:about 1E-5, and most preferably at least 1:about 5E-5.

In case the first catalyst composition comprises P, the molar ratio Co:P is up to 1:about 0.005 (1:about 5E-3; also depicted as: $CoP_c$ wherein c is >0-about 0.005) and preferably up to 1:about 1E-3. Preferably, the molar ratio of Co:P is at least 1:about 1E-6 in case the first catalyst composition comprises P, more preferably at least 1:about 1E-5, and most preferably at least 1:about 5E-5.

The first catalyst composition used in the present invention further may comprise one or more additional elements selected from the group consisting of alkali metal element, alkaline earth metal element and transition metal element (depicted herein as "M"). In the context of the present invention, it was found that $CO_2$ formation and the therewith associated coke deposition by the Boudouard reaction can be suppressed when the first catalyst composition further comprises one or more basic elements selected from the group consisting of alkali metal elements, alkaline earth metal elements and transition metal elements. As used herein, the term "basic element" relates to an element that forms a "Lewis base" (i.e. an element that is able to provide a pair of electrons and thus capable of coordination to a Lewis acid, thereby producing a Lewis adduct) and/or a "Brønsted base" (i.e. an element capable of accepting a proton from a acid or the corresponding chemical species) in the catalyst composition.

Preferably, the one or more alkali metals that may be comprised in the first catalyst composition are selected from the group consisting of sodium (Na), potassium (K), rubidium (Rb) and caesium (Cs), more preferably selected from the group consisting of sodium (Na), potassium (K) and caesium (Cs), and most preferably is potassium (K). The one or more alkaline earth metals that may be comprised in the first catalyst composition are preferably selected from the group consisting of magnesium (Mg), calcium (Ca), strontium (Sr) and barium (Ba), and more preferably selected from the group consisting of magnesium (Mg) and calcium (Ca). The one or more transition metal elements that may be comprised in the first catalyst composition used in the present invention are preferably selected from "Group 4 of the Periodic Table" and more preferably selected from the group consisting of titanium (Ti) and zirconium (Zr).

The amount of alkali metal, alkaline earth metal and/or transition metal elements ("M") that may be comprised in the first catalyst composition used in the present invention is determined by the molar ratio in relation to the cobalt present in the catalyst composition. In case the first catalyst composition comprises M, the molar ratio Co:M is up to 1:about 0.005 (1:about 5E-3; also depicted as: $CoM_d$ wherein d is >0-about 0.005) and preferably up to 1:about 1E-3. Preferably, the molar ratio of Co:M is at least 1:about 1E-6 in case the catalyst composition comprises M, more preferably at least 1:about 1E-5, and most preferably at least 1:about 5E-5.

In this respect, it should be noted that the first catalyst composition of the present invention is a mixed oxide catalyst and not a catalyst wherein the active elements are deposited on a catalyst support. The unsupported catalyst of the present invention is fundamentally different from F-T catalysts wherein Co and Mn are deposited on a (metal) oxide catalyst support. Nevertheless, the catalyst composition may further comprise a (metal) oxide, e.g. as a binder or a diluent.

Accordingly, the first catalyst composition of the present invention may further comprise a binder which preferably is selected from the group consisting of silica, alumina, titanic, zirconium, carbon and zeolite. The zeolite may be a mesoporous zeolite or a microporous zeolite.

The first catalyst composition may be prepared by a method comprising the steps:

(a) preparing a solution of cobalt- and manganese-comprising salts to form a cobalt-manganese-solution;

(b) admixing an alkaline solution to the cobalt-manganese-solution to form a precipitate;

(c) admixing a solution of a lanthanum-comprising salt; and/or a solution of a phosphorus-comprising salt; and preferably a solution of a salt comprising one or more elements selected from the group consisting of alkali metal elements, alkaline earth metal elements and transition metal elements to the solution comprising the precipitate to form a modified precipitate;

(d) separating the modified precipitate from the liquid, washing and drying the modified precipitate to form a dried precipitate;

(e) calcining the dried precipitate in air to form a calcined catalyst precursor; and (f) contacting the calcined catalyst precursor with a reducing agent.

Preferably, the method for preparing the catalyst composition of the invention comprises the steps (a)-(f) in the herein above described order.

In the cobalt-manganese-solution preparation step (a) as described herein, a solution comprising soluble cobalt- and manganese-comprising salts is prepared. The solvent and the obtained solution may be heated to facilitate dissolving of the cobalt- and manganese-comprising salts. Preferably, the solvent and the obtained solution is heated to at least about 60° C. and up to about 95° C. (about 60-95° C.), most preferably to about 80° C.

In the present method for preparing the catalyst composition, the solution may be made in any suitable solvent. Suitable solvents are all compounds in which the chosen salts are soluble and which are easy to remove again in the separation step as defined herein. Aqueous solutions, however, are preferred. Most preferably, the solvent is water ($H_2O$).

In the precipitate forming step (b) as described herein, a precipitate is formed by converting the soluble cobalt- and manganese-comprising salts into insoluble compounds by admixing an alkaline solution, preferably under constant agitation. Preferably, the precipitate is formed by admixing a suitable amount of ammonium hydroxide and/or sodium carbonate solution, preferably ammonium hydroxide solution, to a cobalt-manganese-solution. The amount of alkaline compound present in the alkaline solution is selected so that it is at least sufficient for the stoichiometric reaction with the soluble cobalt- and manganese-comprising salts present. Preferably, the amount of alkaline compound present in the alkaline solution is 1-10 times the stoichiometric required amount. Preferably, the ammonium hydroxide and/or sodium carbonate solution is heated to the same temperature as the cobalt-manganese-solution. The temperature of the mixture may be kept constant until the precipitate is formed under constant agitation.

In the modified precipitate forming step (c) as described herein, a solution of a lanthanum-comprising salt; and/or a solution of a phosphorus-comprising salt; and preferably a solution of a salt comprising one or more elements selected from the group consisting of the alkali metal elements, the alkaline earth metal elements and the transition metal elements is admixed to the solution comprising the precipitate, preferably under continuous agitation, to form a modified precipitate. The solution of a salt comprising one or more elements selected from the group consisting of the alkali metal elements, the alkaline earth metal elements and the transition metal elements is preferably added at the same time or after adding the solution of a lanthanum-comprising salt; and/or a solution of a phosphorus-comprising salt. Most preferably, the solution of a salt comprising one or more elements selected from the group consisting of the alkali metal elements, the alkaline earth metal elements and the transition metal elements is added after adding the solution of a lanthanum-comprising salt; and/or a solution of a phosphorus-comprising salt. The solutions used in the modified precipitate forming step may be made in any suitable solvent. Aqueous solutions, however, are preferred. Most preferably, the solvent is water ($H_2O$).

In the precipitate separation step (d) as described herein, the modified precipitate (i.e. the solid phase of the mixture that is formed after completing the modified precipitate forming step (c)) is separated from the liquid (i.e. the liquid phase of the mixture that is formed after completing the modified precipitate forming step (c)) using any conventional method which allows the separation of a precipitate from a solvent. Suitable methods include, but are not limited to, filtering, decanting and centrifugation. Subsequently the obtained precipitate is washed using the solvent in which the solutions were made, preferably with water, most preferably with distilled water. The modified precipitate is then dried, preferably at about 110-120° C. for about 4-16 hours to form a dried precipitate.

In the calcining step (e) as described herein, the dried precipitate is calcined in air to form a calcined catalyst precursor. Preferably, the dried precipitate is calcined at about 500-600° C. for about 4-24 hours. The calcined but unreduced catalyst mainly comprises the spinel $Co_2MnO_4$.

After calcination, the calcined catalyst precursor is preferably formed into pellets using any conventional method. Said pellets may subsequently be sieved to obtain regularly sized particles. Said particles may be sized between about 0.65-0.85 mm.

In the reducing step (f) as described herein, the calcined catalyst precursor is contacted with a reducing agent. This is to partially reduce the comprised Co to its metallic state and results in the formation of cobalt manganese oxide comprising catalyst as defined herein. In addition thereto, the first catalyst composition comprises metallic Co supported on MnO at the end of the reducing step. Hence, the MnO is not reduced completely into metallic Mn. Accordingly, the first catalyst composition used in the present invention, inter alia comprising metallic cobalt, MnO and mixed spinels having the formula $Co_2MnO_4$ and $Co_2Mn_2O_2$, is obtainable by the herein described method for preparing a catalyst composition after the "reducing step" is finished.

Accordingly, the reducing step is very important for the method for preparing the first catalyst composition of the present invention. When the reducing step is performed too mild, an insufficient amount of Co is reduced to its metallic state. When the reducing step is performed too harsh, the first catalyst composition comprises an insufficient amount of "cobalt manganese oxide" and/or MnO. The skilled person can easily determine that the obtained catalyst composition comprises metallic cobalt, MnO and cobalt manganese oxide by using standard analytical techniques, including X-ray diffraction.

Any suitable reducing agent may be used in the reducing step of this invention. Preferably, the reducing step is performed using a reducing agent in the gas phase. The preferred reducing agent is selected from the group consisting of hydrogen ($H_2$) and carbon monoxide (CO). The reduction can be carried out at ambient temperature or at elevated temperature. Preferably, the reduction is carried out at a temperature of at least about 300° C., more preferably of at least about 350° C. and up to about 500° C., more preferably up to about 450° C. Preferably, calcined catalyst precursor is contacted with a reducing agent for at least about 14 hrs, more preferably for at least about 16 hrs and up to about 24 hrs, more preferably up to about 20 hrs.

Preferably, the reducing step is performed "in situ". The term "in situ" is well known in the field of chemical engineering and refers to industrial plant operations or procedures that are performed in place. For example, aged catalysts in industrial reactors may be regenerated in place (in situ) without being removed from the reactors; see e.g. WO 03/041860 and WO 03/076074. In the context of the present invention, accordingly, a catalyst composition that is reduced in situ refers to a catalyst composition wherein the reducing step is performed in place, i.e. in the same enclosure that is later present in the process installation in which the catalysed process takes place. In one embodiment, the reducing step as defined herein is performed while the "calcined catalyst precursor" is already present in the catalyst enclosure that is situated in the process installation wherein the catalyst composition is to be employed. In a further embodiment, the reducing step as defined herein is performed while the "calcined catalyst precursor" is already present in the catalyst enclosure which can be directly placed into said process installation.

The first catalyst composition may be an unsupported catalyst composition obtainable by the method comprising the steps:

(a) preparing a solution of cobalt- and manganese-comprising salts to form a cobalt-manganese-solution;
(b) admixing to the cobalt-manganese-solution to form a precipitate;
(c) admixing a solution of a lanthanum-comprising salt; and/or a solution of a phosphorus-comprising salt; and preferably a solution of a salt comprising one or more elements selected from the group consisting of alkali metal elements, alkaline earth metal elements and transition metal elements to the solution comprising the precipitate to form a modified precipitate;
(d) separating the modified precipitate from the liquid, washing and drying the modified precipitate to form a dried precipitate;
(e) calcining the dried precipitate in air to form a calcined catalyst precursor; and
(f) contacting the calcined catalyst precursor with a reducing agent.

The terms "aliphatic hydrocarbons" and "aromatic hydrocarbons" are very well known in the art. Accordingly, an "aliphatic hydrocarbons" relates to acyclic or cyclic, saturated or unsaturated hydrocarbon compounds that are not aromatic hydrocarbons. The term "aromatic hydrocarbons" relates to cyclically conjugated hydrocarbons with a stability (due to delocalization) that is significantly greater than that of a hypothetical localized structure (e.g. Kekulé structure). The most common method for determining aromaticity of a given hydrocarbon is the observation of diatropicity in the $^1$H NMR spectrum.

In the context of the present invention, it was surprisingly found that substantially no waxes are produced in the process for Fischer-Tropsch synthesis of the present invention. Moreover, it was found that the selectivity for lower hydrocarbons having between 2 and 5 carbon atoms (C2-C5 HC) and aromatic hydrocarbons is increased.

In the process of the present invention, the first catalyst composition is preferably comprised in a fixed bed reactor or a fluidized bed reactor.

In a further embodiment, the present invention relates to the process for producing ethylene and propylene as described above comprising the method for preparing the first catalyst composition as described herein.

In the present invention, the first product stream is preferably produced by Fischer-Tropsch synthesis.

Syngas

Preferably, the syngas has a hydrogen ($H_2$) to carbon monoxide (CO) molar ratio of about 1-4 (i.e. $H_2$:CO is 1:about 1-4). The term "syngas" as used herein relates to a gaseous mixture substantially consisting of hydrogen ($H_2$) to carbon monoxide (CO). The syngas, which is used as a feed stream to the present process, may comprise up to 10 mol-% of other components such as $CO_2$ and lower hydrocarbons (lower HC). Said other components may be side-products or unconverted products obtained in the process used for producing the syngas. Preferably, the syngas comprises substantially no molecular oxygen ($O_2$). As used herein, the term "syngas comprising substantially no $O_2$" relates to a syngas which comprises such a low amount of $O_2$ so that the comprised $O_2$ does not interfere with the Fischer-Tropsch synthesis reaction. Preferably, the syngas comprises not more than 1 mol-% $O_2$, more preferably not more than 0.5 mol-% $O_2$ and most preferably not more than 0.4 mol-% $O_2$.

The process conditions useful in the process of the present invention can be easily determined by the person skilled in the art; for step a), see Dry (2004) Stud. Surf. Sci. Catal 152:197-230 in "Fischer-Tropsch technology" eds. Steynberg and Dry. Accordingly, the Fischer-Tropsch synthesis is performed at a reaction temperature of about 150-350° C., a space velocity of about 400-5000 $h^{-1}$, preferably of about 2000 $h^{-1}$ and a pressure of between atmospheric and about 5 MPa. The first catalyst composition may be stabilized for about 80-100 hours at about 150-350° C. before actual use.

In this respect, it should be noted that the reaction conditions have a marked effect on the catalytic performance. It has been reported that selectivity on a carbon basis is essentially a function of the probability of chain growth, a; see Dry (2004) loc. cit. Control of the product selectivity is to a large extent determined by the factors that influence the value of a. The main factors are the temperature of the reaction, the gas composition and more specifically the partial pressures of the various gases in contact with catalyst inside the reactor. Overall, by manipulating these factors a high degree of flexibility can be obtained regarding the type of product and the carbon range. An increase in FT-synthesis operating temperature shifts the selectivity profile to lower carbon number products. Desorption of growing surface species is one of the main chain termination steps and since desorption is an endothermic process so a higher temperature should increase the rate of desorption which will result in a shift to lower molecular mass products. Similarly, the higher the CO partial pressure the more is the catalyst surface covered by adsorbed monomers. The lower the coverage by partially hydrogenated CO monomers the higher the probability of chain growth is expected to be; see also Mirzaei et al., Adv. Phys. Chem., 2009, 1-12. Accordingly, the two key steps leading to chain termination are desorption of the chains yielding alkenes and hydrogenation of the chains to yield alkanes.

Second Catalyst Composition

According to the process of the present invention, the second product stream is converted into a fourth product stream comprising ethylene and/or propylene. This is preferably performed by contacting the second product stream with a second catalyst composition suitable for converting aliphatic hydrocarbons having 4 or more carbon atoms into ethylene and/or propylene. Preferably, the second catalyst composition is an olefin metathesis catalyst suitable for converting 1-butylene and 1-hexene into ethylene and propylene.

Suitable examples for the second catalyst composition include an olefin metathesis catalyst. Examples of suitable catalysts are described e.g. in U.S. Pat. No. 6,586,649, which is incorporated herein by reference in terms of the catalyst:

The second catalyst composition may be at least one metal oxide selected from the group consisting of the oxides of the transition metals.

The transition metal oxide catalyst in the second catalyst composition is preferably selected from oxides of molybdenum, or of rhenium or of tungsten, or of mixtures of any two or more of tungsten, rhenium and molybdenum. This catalyst may be a homogeneous (unsupported) catalyst or a heterogeneous (supported) catalyst. The catalyst is preferably supported and any convenient support may be used, provided it neither interferes with nor inhibits the metathesis step of the process according to the invention. Suitable supports include those based on or including ceramic supports such as silica, alumina, titania, zirconia or mixtures thereof, with silica being preferred. The catalyst can be attached to its support in any convenient fashion, such as those known in the art, in particular by sublimation or by wet impregnation. The transition metal oxide constituent of the catalyst may amounts to 1-30% by mass of the total catalyst mass (transition metal and support together), preferably 6-20% thereof. In particular the catalyst may be a $WO_3$-based (tungsten oxide-based) catalyst containing Cs (caesium) as a promoter.

In the cases where the second catalyst composition is a supported catalyst type, the transition metal oxide may form e.g. 1-30% by mass of the total heterogeneous catalyst mass. In particular, the catalyst of the heterogeneous catalyst mass may consist essentially of tungsten oxide, being supported on silica, the catalyst mass containing a promotor selected from the group consisting of cesium (to decrease selectivity towards propylene) and phosphates (to increase selectivity towards propylene).

Preferably the second catalyst composition has as high a proportion of acid sites thereon as practicable. Acidity of the catalyst can be enhanced by treating the catalyst with organic acids or inorganic acids, or by impregnation thereof with cations such as those of phosphates or borates. Acidity of the catalyst can, conversely, be reduced by blocking acid sites thereon, by means of alkaline earth metals.

Many other suitable olefin metathesis catalysts are known, for example as described in U.S. Pat. No. 8,153,851 and U.S. Pat. No. 5,990,369.

MODE(S) FOR CARRYING OUT THE INVENTION

The present invention will now be more fully described by the following non-limiting Examples and figures.

Figure 1:
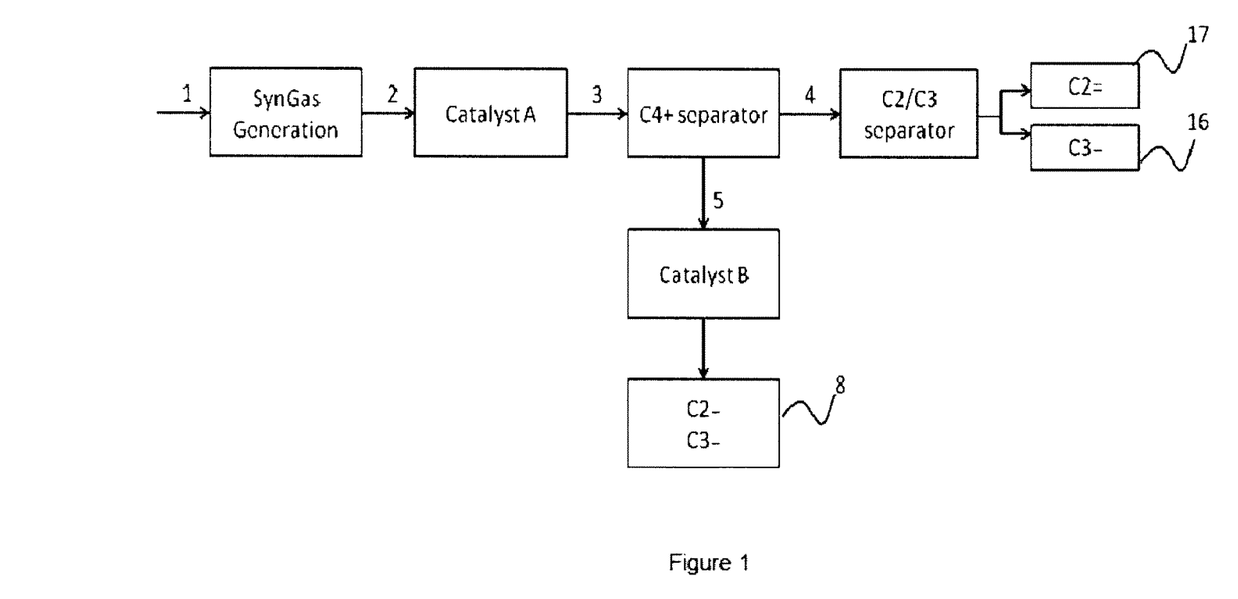
FIG. 1 shows a scheme of an embodiment of the process according to the present invention.

In FIG. 1, feedstock 1 such as natural gas, coal, biomass or municipal solid waste is fed to the syngas generation unit. The syngas generated 2 is contacted with a first catalyst composition (catalyst A) to obtain a first product stream 3 comprising ethylene and propylene and aliphatic hydrocarbons having 4 or more carbon atoms. The first product stream 3 is fed to a C4+ separator to split the first product stream 3 into a second product stream 5 comprising at least 90 wt % of said aliphatic hydrocarbons having 4 or more carbon atoms and a third product stream 4 comprising ethylene and propylene.

The third product stream 4 is fed to a C2/C3 separator to separate ethylene and propylene in the third product stream 4. A first ethylene stream 17 and a first propylene stream 16 are obtained.

The second product stream 5 is contacted with a second catalyst composition (catalyst B) so that a fourth product stream 8 comprising ethylene and/or propylene is produced.

Figure 2:
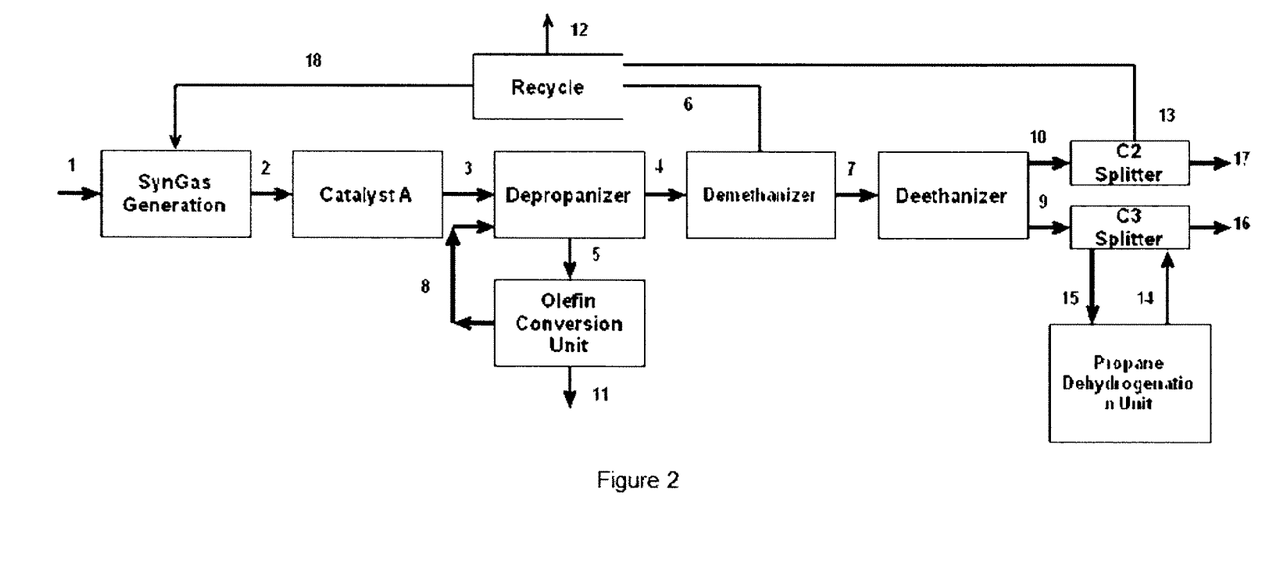
FIG. 2 shows a further embodiment of the process according to the present invention.

FIG. 2 shows a further embodiment of the process according to the present invention. Feedstock 1 is fed to the syngas generation unit which produces syngas 2. The syngas 2 is contacted with the first catalyst composition (catalyst A) to obtain a first product stream 3. The first product stream 3 is fed to the depropanizer to split the first product stream 3 into a second product stream 5 comprising at least 90 wt % of the aliphatic hydrocarbons having 4 or more carbon atoms and a third product stream 4 comprising ethylene and propylene.

The second product stream 5 is contacted with a second catalyst composition in the olefin conversion unit, which produces a fourth product stream 8 comprising ethylene and propylene and a product stream 11 comprising BTX. The fourth product stream 8 is fed back to the depropanizer and is mixed with the first product stream 3.

The third product stream 4 is fed to the demethanizer and methane 6 is removed from the third product stream 4, producing a fifth product stream 7 which essentially consists of ethane, ethylene, propane and propylene. Methane 6 is fed to the recycle unit, which removes undesired components 12 and feeds the remainder 18 to the syngas generation unit.

The fifth product stream 7 is fed to the deethanizer and is separated into a sixth product stream 10 comprising ethane and ethylene and a seventh product stream 9 comprising propane and propylene.

The sixth product stream 10 is fed to the C2 splitter, which separates ethane 13 and ethylene 17. Ethane 13 is fed to the recycle unit, which removes undesired compounds 12 and feeds the remainder 18 to the syngas generation unit.

The seventh product stream 9 is fed to the C3 splitter, which separates propane 15 and propylene 16. Propane 15 is fed to the propane dehydrogenation unit, which dehydrogenates propane into propylene 14. Propylene 14 is fed back to the C3 splitter.

EXAMPLE 1

Ethylene and propylene were produced from syngas according to the scheme as illustrated in FIG. 2.

A catalyst composition as generally described under the section 'first catalyst composition' was used as the first catalyst composition (catalyst A), i.e. the first catalyst composition used is unsupported and comprises cobalt; manganese; and at least one element selected from the group of lanthanum and phosphorus, wherein the relative molar ratios of the elements comprised in said composition are represented by the formula $$CoMn_aLa_bP_cM_dO_x$$

wherein:

M is one or more elements selected from the group consisting of alkali metal, alkaline earth metal and transition metal;

a is about 0.8-1.2;

b and/or c is >0-about 0.005;

d is 0-about 0.005; and x is a number determined by the valence requirements of the other elements present.

The obtained first product stream had a composition as shown in Table 1.

The aliphatic hydrocarbons having 4 or more carbon atoms (indicated as C4+) was fed to an olefin conversion unit. The obtained product stream contained a major amount of ethylene and propylene and a minor amount of BTX, as can be seen in Table 1.

Hence, the total amount of the obtained ethylene and propylene significantly increased by the conversion of C4+ into ethylene and propylene compared to the case in which only the first catalyst composition was used.

TABLE 1

|  | Syngas Feed Kg/hr | First product stream Kg/hr | Feed to olefin conversion unit Kg/hr | Products of olefin conversion unit Kg/hr | Total Kg > hr | % Increase |
|---|---|---|---|---|---|---|
| Ar |  |  |  |  |  |  |
| CO | 206938 | 16063 |  |  |  |  |
| H2 | 41870 | 23892 |  |  |  |  |
| N2 | 560 | 560 |  |  |  |  |
| CO2 |  | 5149 |  |  |  |  |
| C2 |  | 2571 |  |  |  |  |
| C2= |  | 16994 |  |  | 12024 | 29018 |
| C3 |  | 2231 |  |  |  |  |

TABLE 1-continued

| | Syngas Feed Kg/hr | First product stream Kg/hr | Feed to olefin conversion unit Kg/hr | Products of olefin conversion unit Kg/hr | Total Kg > hr | % Increase |
|---|---|---|---|---|---|---|
| C3= | | 25492 | | 18041 | 43533 | |
| C4+ | | 37570 | 37570 | | | |
| BTX | | | | 340 | | |
| total | | 130522 | 37570 | 30065 | | |
| Total C2 C3 olefins | | 42486 | | | 72551 | 70.8 |

EXAMPLE 2

In this example, propane obtained by C3 splitter was fed to a propane dehydrogenation unit. This resulted in an even higher amount of propylene in the final product, as shown in Table 2.

TABLE 2

| | Syngas Feed Kg/hr | First product stream Kg/hr | Feed To olefin conversion unit Kg/hr | Products of olefin conversion unit Kg/hr | Feed to PDH | PDH Product | Total Kg/hr | % Increase |
|---|---|---|---|---|---|---|---|---|
| Ar | | | | | | | | |
| CO | 206938 | 16063 | | | | | | |
| H2 | 41870 | 23892 | | | | | | |
| N2 | 560 | 560 | | | | | | |
| CO2 | | 5149 | | | | | | |
| C2 | | 2571 | | | | | | |
| C2= | | 16994 | | 12024 | | | 29018 | |
| C3 | | 2231 | | | 2231 | | | |
| C3= | | 25492 | | 18041 | | 2130 | 45663 | |
| C4+ | | 37570 | 37570 | | | | | |
| BTX | | | | 340 | | | | |
| total | | 130522 | 37570 | 30065 | | | | |
| Total C2 C3 olefins | | 42486 | | | | | 74681 | 75.8 |

The invention claimed is:

1. A process for producing ethylene and propylene from syngas, the process comprising the steps of
   a) contacting syngas with a first catalyst composition to obtain a first product stream comprising ethylene, propylene and aliphatic hydrocarbons having 4 or more carbon atoms,
   b) splitting the first product stream into
      a second product stream comprising at least 90% of said aliphatic hydrocarbons having 4 or more carbon atoms and
      a third product stream comprising ethylene and propylene,
   c) separating ethylene and propylene in the third product stream so as to form a first ethylene stream and a first propylene stream and
   d) converting the second product stream into a fourth product stream comprising ethylene and/or propylene,
   wherein the first catalyst composition is unsupported and comprises cobalt manganese; and at least one of lanthanum and/or phosphorus, wherein the relative molar ratios of the elements comprised in said composition of formula $$CoMn_aLa_bP_cM_dO_x$$

wherein:
   M is one or more elements selected from the group consisting of alkali metal, alkaline earth metal, and transition metal;
   a is about 0.8-1.2;
   b and/or c is >0-about 0.005;
   d is 0-about 0.005; and
   x is a number determined by the valence requirements of the other elements present.

2. The process according to claim 1, wherein the fourth product stream comprising ethylene and/or propylene is mixed with the first product stream.

3. The process according to claim 1, wherein the first product stream and the third product stream further comprise methane, ethane and propane and wherein step c) comprises the steps of:
   c1) removing methane from the third product stream to obtain a fifth product stream comprising ethane, ethylene, propane and propylene,
   c2) separating the fifth product stream into a sixth product stream comprising ethane and ethylene and a seventh product stream comprising propane and propylene,
   c3) removing ethane from the sixth product stream to form the first ethylene stream and
   c3') removing propane from the seventh product stream to form the first propylene stream.

4. The process according to claim 3, wherein propane removed from the seventh product stream in step c3') is dehydrogenated into propylene and mixed with the seventh product stream.

5. The process according to claim 3, wherein methane removed from the third product stream of step c1) is added to the syngas.

6. The process according to claim 3, wherein ethane removed from the sixth product stream in step c3) is added to the syngas.

7. The process according to claim 1, wherein M is selected from the group consisting of sodium (Na), potassium (K), rubidium (Rb), cesium (Cs), magnesium (Mg), calcium (Ca), strontium (Sr), barium (Ba), titanium (Ti), and zirconium (Zr).

8. The process according to claim 1, wherein the first catalyst composition comprises cobalt; manganese; lanthanum; and phosphorus, wherein:
b is >0-about 0.005; and
c is >0-about 0.005.

9. The process according to claim 1, wherein the first catalyst composition is comprised in a fixed bed reactor or fluidized bed reactor.

10. The process according to claim 1, wherein the syngas has a hydrogen ($H_2$) to carbon monoxide (CO) molar ratio of about 1-4.

11. The process according to claim 1, wherein step d) is performed by contacting the second product stream with a second catalyst composition which is an olefin metathesis catalyst suitable for converting 1-butylene and 1-hexene into ethylene and propylene.

12. The process according to claim 11, wherein the second catalyst composition comprises an oxide selected from the group consisting of the oxides of molybdenum, the oxides of rhenium, the oxides of tungsten, and mixtures thereof.

13. The process according to claim 1, wherein the first product stream is produced by Fischer-Tropsch synthesis.

14. The process according to claim 13, wherein said Fischer-Tropsch synthesis is performed at a reaction temperature of about 150-350° C., a space velocity of about 400-5000 $h^{-1}$ and a pressure of between atmospheric and about 5 MPa.

* * * * *